(12) United States Patent
Summers

(10) Patent No.: US 6,733,797 B1
(45) Date of Patent: May 11, 2004

(54) NEUROCEUTICAL FOR IMPROVING MEMORY AND COGNITIVE ABILITIES

(76) Inventor: William K. Summers, 2400 Louisiana, NE., Suite 530, Albuquerque, NM (US) 87110

(*) Notice: Subject to any disclaimer, the term of this patent is extended or adjusted under 35 U.S.C. 154(b) by 0 days.

(21) Appl. No.: 09/992,132

(22) Filed: Nov. 15, 2001

Related U.S. Application Data

(60) Provisional application No. 60/249,046, filed on Nov. 15, 2000.

(51) Int. Cl.$^7$ ................................................ A61K 35/78
(52) U.S. Cl. ...................... 424/728; 424/736; 424/752; 424/756; 424/766
(58) Field of Search ................................ 424/728, 736, 424/752, 756, 766

(56) References Cited

U.S. PATENT DOCUMENTS

| | | | |
|---|---|---|---|
| 4,474,773 A | * | 10/1984 | Shinitzky et al. |
| 4,780,456 A | | 10/1988 | Pistolesi |
| 5,043,323 A | * | 8/1991 | Bombardelli et al. |
| 5,214,180 A | | 5/1993 | Ferrari et al. |
| 5,428,026 A | | 6/1995 | Colarow |
| 5,648,377 A | * | 7/1997 | Bombardelli et al. |
| 5,800,835 A | | 9/1998 | Zastrow et al. |
| 5,994,322 A | | 11/1999 | Masuda et al. |
| 6,048,846 A | | 4/2000 | Cochran |
| 6,103,746 A | | 8/2000 | Yarosh |
| 6,117,853 A | | 9/2000 | Sakai et al. |

OTHER PUBLICATIONS

Castleman (The Healing Herbs (1991), Rodale Press: Pennsylvania; Barberry, pp. 59–61; Ginseng, pp. 193–200; Gotu Kola, pp. 205–208; and Tumeric. pp. 355–357).*

Halliwell. B., et al., "Free Radicals in Biology and Medicine." 1$^{st}$ Ed., Oxford Univ Press. p. 279 Chapter 8 (1985).

Halliwell. B., et al., "Free Radicals in Biology and Medicine," 2$^{nd}$ Ed., Oxford Univ Press, pp. 416–422 (Chapter 8)(1989).

Halliwell. B., et al., "Free Radicals in Biology and Medicine," 3$^{rd}$ Ed., Oxford Univ Press, pp 618–624 (Chapter 9) (1999).

Halliwell. B., et al., "Free Radicals in biology and Medicine". 3$^{rd}$ Ed., Oxford Press pp 736–760 (1999).

Hildebrand. D.H., et al., "Phospholipids Plus Tocopherols Increase Soybean Oil Stability," JAOCS. vol. 61, No. 3, pp. 552–555 (1984).

Joaquin. A.N. et al., "Functional Decline in Aging and Disease: A Role for Apoptosis." JAGS. vol. 49, pp 1234–1240 (2001).

Sardi, B., "What's bBest in Multi–Vitamin." 2$^{nd}$ Ed (1999) San Dimas CA. Sardi Publications. pp 67–77.

Summers, W.K., "Correspondence: Oral Tetrahydroaminoacridine in the Treatment of Senile Dementia. Alzheimer's Type." New England Journal of Medicine, vol. 316. p. 1605, (1987).

Tesoriere, I . . . et al., "Synergistic Interactions Between Vitamin A and Vitamin E against Liped Peroxidation in Phosphatidylcholine Liposomes," Archives of Biochemistry and Biophysics, vol. 326, No. 1. pp 57=63 (Feb. 1, 1996) Article No. 0046.

Garry Null's Nutritional Products: Supreme Health Formula. Advertisement www.naturalliving.com products supremehealth.htm–Jun. 2000.

* cited by examiner

Primary Examiner—Francisco Prats
Assistant Examiner—Susan D. Coe
(74) Attorney, Agent, or Firm—Deborah A. Peacock

(57) ABSTRACT

The present invention relates to a neurochemical formulation comprising a supplement for improving function of neurons, improving memory and cognitive abilities, and reversing free radical damage caused by aging or neurodegenerative disease. The formulation comprises phosphoesters and antioxidants. Components may have antioxidant properties or enhance properties of other components. The synergistic combinations allow individual component dosages to be reduced, thereby minimizing potential toxicity.

44 Claims, No Drawings

NEUROCEUTICAL FOR IMPROVING MEMORY AND COGNITIVE ABILITIES

CROSS-REFERENCE TO RELATED APPLICATIONS

This application claims the benefit of the filing of U.S. Provisional Patent Application Serial No. 60/249,046, entitled "Neurochemical for Improving Memory and Cognitive Abilities," filed on Nov. 15, 2000, and the specification thereof is incorporated herein by reference.

BACKGROUND OF THE INVENTION

1. Field of the Invention (Technical Field)

This invention relates to health supplement compositions, specifically those utilizing antioxidants or phosphatides, and their use.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Health supplements are used by millions of Americans everyday, ranging from single ingredient vitamin supplements to multi-vitamins to prescription supplements incorporating hormone therapy and other medicinal treatments. A broad number of these health supplements are readily available to the public in over-the-counter formulations, many touting condition specific uses, such as the recent spate of "ultimate anti-aging formulations." One of these formulations contains 65 components and suggests ingestion of over 10,000 mg of the combination per day which, due to limitations of tablet size, requires ingesting ten tablets each day. More popular brands of multivitamins contain between 26 ingredients (Theragran-M—by Mead Johnson) and 53 ingredients (Maxilife Phyto—by Twinlab). These "shotgun" approaches of incorporating all possible useful ingredients face not only serious criticisms, but also present serious potential dangers to a user. (See, Sardi, B. "What's Best in a Multivitamin," 2d Ed. (1998), San Dimas, Calif., Sardi Publications, pp. 67–77.) For example, riboflavin (vitamin $B_2$) is known to be toxic in doses above 10 mg per day. Many supplement formulations exceed this limit, posing a potential health risk to the users.

Many health supplement formulations include substantial numbers of herbal compounds. Herbal compounds naturally contain numerous active chemical groups. These active chemical groups compete for overall effect. For example, lemon fruit has an acid content, but counterintuitively, has an alkaline effect within the human body. Grapefruit contains antioxidant herbal substances which can interfere with drugs such as felodipine (Plendil®) or nifedipine (Procardia®). It is intuitive that indiscriminate combinations of numerous herbs, each containing numerous key constituents, might have a subtractive overall effect. Garlic is often used in formulations for its antioxidant properties, but may have the side effect of combining with other components in the formulation to exceed safe limits of selenium (200 mcg/day), due to garlic's relatively high selenium content. Therefore, many supplements on the market incorporating herbal compounds may be more harmful than "healthful."

One promising way to incorporate important supplement components while reducing the potential for high dose toxicity is to utilize synergistic relationships among components. "Pharmacologic synergy" is a complementary, superadditive response resulting from the combination of two or more agents. For example, there are numerous examples of synergy between antioxidant vitamins. U.S. Pat. No. 5,994,322 to Masuda cites a lecithin-vitamin $B_{12}$ combination as synergistic. The oxidative synergy of vitamin E and phospholipid have been demonstrated as better than vitamin E alone. (See, Tesories, L., et al., "Synergistic Interactions Between Vitamin A and Vitamin E Against Lipid Peroxidation in Phosphatidylcholine Liposomes," Archives Biochemistry Biophysiology, (1996), vol. 326(1), pp. 57–63.) Vitamin A and vitamin E have more antioxidant synergy with phosphatidylcholine liposomes than the respective single components. Other studies on synergy between numerous compounds for a focused outcome are surprisingly sparse.

On the flip side, other supplement formulations do not provide enough of certain supplements. Although many health supplements contain choline, a member of the B vitamin group, their formulations do not adequately address the needs created by phospholipid physiology. Phosphatidylcholine (either as a phosphomonoester or phosphodiester), is the serum transport form of choline. As can be seen in FIG. 1, phosphatidylcholine (monoester form) has a substitution on either $R_1$ or $R_2$, but not on both. (Choline is depicted for comparison to phosphatidylcholine.) This form of choline is a principle component of all cell membranes. It is especially important to have a sufficient amount of phosphatidylcholine to maintain intact nerve cell membranes. For example, cholinergic nerve cells in particular, when faced with a reduced level of serum phosphatidylcholine, will resort to autocannibalism of the phosphatidylcholine in their cell membranes to maintain their primary mission: producing the neurotransmitter acetylcholine. This degenerates nerve cell membranes, resulting in conditions such as Alzheimer's Disease related dementia. (See, Summers, W. K. Correspondence: Oral Tetrahydroaminoacridine in the Treatment of Senile Dementia, Alzheimer's Type, New England Journal of Medicine, vol. 316, p. 1605, (1987).) The choline in phosphatidylcholine is also the principle source of choline metabolized into two other forms of phosphatides: sphingolipids and plasmalogens. Both of these forms are necessary for proper function of the central nervous system.

One of the more important focuses of health supplements is the reduction of free radicals. Free radicals are associated with aging of the brain. (See, Halliwell, B., Gutteridge, J. M. C. "Free Radicals in Biology and Medicine" ($3^{rd}$ ed.), (1999) New York, Oxford University Press.) Oxidative injury to the nervous system has been documented in diseases such as AIDS-associated dementia, Alzheimer's disease, benign senile forgetfulness (pre-Alzheimer's disorder), Down's syndrome-associated dementia, Lewy body dementia, multi-infarct dementia, multiple sclerosis, Parkinson's disease-associated dementia, tardive dyskinesia, Wernicke-Korsakoff syndrome, and alcoholism-associated dementia. Indeed, oxidative injury may be the final common pathway leading to cell death. (See, Joaquin, A. M. et al., "Functional Decline in Aging and Disease: A Role for Apoptosis," Journal American Geriatrics Society, (2001), vol. 49, pp. 1234–1240.) Numerous studies have shown benefit from the use of antioxidants in many of these disorders. (See, Halliwell, B., Gutteridge, J. M. C., "Free Radicals in Biology and Medicine" ($3^{rd}$ ed.), (1999) New York, Oxford University Press.)

Antioxidants are substances that protect against oxidative stress damage caused by free radicals. There are four generally recognized groups of antioxidants: plant extracts, vitamins, amino acids, and minerals. Vitamins are organic substances provided in relatively small quantities from the environment that are necessary for the maintenance of health. Precursors (e.g., carotene for vitamin A), vitamins having multiple forms (e.g., pyridoxine, pyridoxal, pyridoxamine), and essential oligopeptides are typically referred to as "vitamers," hereinafter to be understood as interchangeable with the term "vitamin."

As discussed above, prior art supplement compositions generally take a "shotgun" approach of providing supplements instead of providing specific formulations for other than a generalized "anti-aging" or "energy" formulation. However, U.S. Pat. No. 6,048,846 to Cochran discloses a combination of supplement components designed to fight the causes of disease. The essential combination disclosed is use of at least one hormone with the supplement components. However, hormone administration can be dangerous given the potential downstream effects. This is the result of interaction with other hormones in feedback systems. The dosage range of hormones is often specific to timing of administration within the relevant physiological cycle. The '846 Patent formulation also does not necessarily result in an antioxidant net effect. For example, iron is used as a preferred mineral. Iron easily forms free radicals. Therefore, iron inclusion can cause a reduction in available antioxidants.

The present invention overcomes the problems associated with a "shotgun" supplement approach. The dosage ranges and use of synergistic component relationships overcome problems with potential toxicity. Additionally, as a targeted composition specific to neuroceuticals, the present invention provides appropriate dosages for treatment and reversal of the effects of neurological disorders in addition to addressing the causes. There is a long-felt need in the art for a supplement composition that addresses ongoing neurological degeneration while avoiding toxic dosages of supplements.

SUMMARY OF THE INVENTION
(DISCLOSURE OF THE INVENTION)

Surprisingly, and contrary to the teachings of the prior art, certain combinations of substances are found to give improved nervous system function with improved cognitive function and mental energy. The present invention is a supplement combination including at least one, and preferably at least two, phosphoesters and at least one antioxidant, preferably comprising at least one but not more than five antioxidant amino acids and at least one but not more than fifteen antioxidant vitamins and at least one antioxidant mineral.

The composition of the present invention exhibits synergistic antioxidant and restorative effects on the nervous system effective in treating neurodegenerative disorders where oxidative injury is believed to be contributory. These synergistic effects additionally allow use of lower doses of most of the individual components.

The present invention is a health supplement composition for mammals comprising at least one phosphoester and at least one synergistic antioxidant combination, wherein the synergistic antioxidant combination comprises at least one antioxidant and at least one other composition component that has a synergistic relationship with the antioxidant.

The composition of the present invention comprises at least one application method selected from the group consisting of oral, parenteral, rectal, and topical administration.

Further, administration on mammals comprises prevention or treatment of illnesses selected from the group consisting of AIDS-associated dementia, Alzheimer's disease, benign senile forgetfulness, Down's syndrome-associated dementia, Lewy body dementia, multi-infarct dementia, multiple sclerosis, Parkinson's disease-associated dementia, tardive dyskinesia, Wernicke-Korsikoff syndrome, and alcoholism-associated dementia.

The phosphoester of the composition of the present invention is selected from the group consisting of phoshatidylcholine, phosphatidylserine, phosphatidylethanolamine and phosphatidylinositol. Preferably, two phosphoesters are used in the composition.

The antioxidant combination of the present invention comprises at least one member selected from the group of antioxidants consisting of herbal, amino acid, mineral, and vitamin antioxidants. The herbal antioxidant comprises at least one member selected from compounds derived from the group consisting of citrus fruits, citrus peels, curcuma, ginkgo biloba, ginseng, gotu kola, proanthocyanidins, quercetin, and Siberian ginseng. The amino acid antioxidant comprises at least one member selected from the group consisting of acetyl-L-camitine, L-glutamine, N-acetyl-L-cystine, L-lysine, L-methionine, and L-taurine. The antioxidant vitamin comprises at least one member selected from the group consisting of vitamin A, vitamin $B_1$, vitamin $B_2$, vitamin $B_3$, vitamin $B_5$, vitamin $B_6$, vitamin $B_{12}$, beta-carotene, vitamin C, vitamin E, L-glutathione, lipoic acid, lutein, lycopene, ubiquinone, and zeaxanthin. The antioxidant mineral comprises at least one member selected from the group consisting of boron, chromium, manganese, magnesium, selenium, and zinc.

The phosphoester of the composition may comprise a daily dosage of between approximately 0 mg and approximately 16,000 mg of phosphatidylcholine, between approximately 0 mg and approximately 300 mg of phosphatidylserine, between approximately 0 mg and approximately 500 mg of phosphatidylethanolamine, and between approximately 0 mg and approximately 10,000 mg of phosphatidylinositol. The phosphoester of the composition preferably comprises a daily dosage of between approximately 0 mg and approximately 1000 mg of phosphatidylcholine, between approximately 0 mg and approximately 100 mg of phosphatidylserine, between approximately 0 mg and approximately 200 mg of phosphatidylethanolamine, and between approximately 0 mg and approximately 1000 mg of phosphatidylinositol.

The herbal antioxidant of the composition comprises a daily dosage of between approximately 0 mg and approximately 7 mg of barberry, between approximately 0 mg and approximately 70 mg of bilberry proanthocyanidins, between approximately 0 mg and approximately 150 mg of lemon bioflavinoids, between approximately 0 mg and approximately 150 mg of lime bioflavinoids, between approximately 0 mg and approximately 150 mg of orange bioflavinoids, between approximately 0 mg and approximately 1000 mg of curcuma, between approximately 0 mg and approximately 2 mg of garlic bioflavinoids, between approximately 0 mg and approximately 180 mg of ginko biloba, between approximately 0 mg and approximately 2000 mg of ginseng, between approximately 0 mg and approximately 100 mg of gotu kola, between approximately 0 mg and approximately 1000 mg of grape seed proanthocyanidins, between approximately 0 mg and approximately 1000 mg of red apple quercetin, between approximately 0 mg and approximately 1000 mg of red onion quercetin, and between approximately 0 mg and approximately 400 mg of Siberian ginseng. The herbal antioxidant preferably comprises a daily dosage of between approximately 0 mg and approximately 35 mg of barberry, between approximately 0 mg and approximately 35 mg of bilberry proanthocyanidins, between approximately 0 mg and approximately 75 mg of lemon bioflavonoids, between approximately 0 mg and approximately 75 mg of lime bioflavonoids, between approximately 0 mg and approximately 75 mg orange bioflavonoids, between approximately 0 mg and approximately 500 mg of curcuma, between approximately 0 mg and approximately 1 mg of garlic bioflavonoid, between approximately 0 mg and approximately 250 mg of ginkgo biloba, between approximately 0 mg and approximately 1000 mg of ginseng, between approximately 0 mg and approximately 50 mg of gotu kola, between approximately 0 mg and approximately 500 mg of grape seed proanthocyanidins, between approximately 0 mg and approximately 500 mg of red apple quercetin, between approximately 0 mg and approximately 500 mg of red onion quercetin, and between approximately 0 mg and approximately 200 mg Siberian ginseng.

The antioxidant amino acid of the composition comprises a daily dosage of between approximately 0 mg and approximately 1500 mg of acetyl-L-carnitine, between approximately 0 mg and approximately 1500 mg of L-glutamine, between approximately 0 mg and approximately 1500 mg of L-lysine, between approximately 0 mg and approximately 1500 mg of L-methionine, between approximately 0 mg and approximately 1500 mg of L-taurine, between approximately 0 mg and approximately 1500 mg of N-acetyl-L-cystine, and between approximately 0 mg and approximately 800 mg S-adenosylmethionine. The antioxidant amino acid preferably comprises a daily dosage of between approximately 0 mg and approximately 800 mg of acetyl-L-carnitine, between approximately 0 mg and approximately 800 mg of L-glutamine, between approximately 0 mg and approximately 800 mg of L-lysine, between approximately 0 mg and approximately 800 mg of L-methionine, between approximately 0 mg and approximately 800 mg of L-taurine, between approximately 0 mg and approximately 800 mg of N-acetyl-L-cystine, and between approximately 0 mg and approximately 800 mg of S-adenosylmethionine.

The antioxidant vitamin of the composition comprises a daily dosage of between approximately 0 mg and approximately 50,000 IU of beta carotene, between approximately 0 mg and approximately 10,400 IU of vitamin A, between approximately 0 mg and approximately 1000 mg of vitamin $B_1$, between approximately 0 mg and approximately 10 mg of vitamin $B_2$, between approximately 0 mg and approximately 1000 mg of vitamin $B_3$, between approximately 0 mg and approximately 500 mg of vitamin $B_5$, between approximately 0 mg and approximately 500 mg of vitamin $B_6$, between approximately 0 mg and approximately 500 mg of vitamin $B_6$ (pyridoxal 5'-phosphate), between approximately 0 mg and approximately 1000 mg of vitamin $B_{12}$, between approximately 0 mg and approximately 3000 mg of vitamin C, between approximately 0 mg and approximately 800 mg of vitamin E, between approximately 0 mg and approximately 1000 mcg of folic acid, between approximately 0 mg and approximately 2000 mg of L-glutathione, between approximately 0 mg and approximately 400 mg of lipoic acid between approximately 0 mg and approximately 30 mg of lutein, between approximately 0 mg and approximately 15,000 mcg of lycopene, between approximately 0 mg and approximately 600 mg of ubiquinone, and between approximately 0 mg and approximately 500 mg of zeaxanthin.

The antioxidant mineral of the composition comprises a daily dosage of between approximately 0 mg and approximately 100 mcg of boron, between approximately 0 mg and approximately 200 mcg of chromium, between approximately 0 mg and approximately 50 mg of manganese, between approximately 0 mg and approximately 1000 mg of magnesium, between approximately 0 mg and approximately 200 mcg of selenium, and between approximately 0 mg and approximately 100 mg of zinc.

The composition may additionally comprise at least one component selected from the group consisting of Bomelain, papain, and betaine. These may comprise a daily dosage of between approximately 0 mg and approximately 80 mg of Bohemian, between approximately 0 mg and approximately 50 mg of papain, and between approximately 0 mg and approximately 50 mg of beeline.

The resultant synergistic antioxidant compound may comprise at least one phosphoester and at least one herbal antioxidant, at least one phosphoester and at least one antioxidant mineral; at least one phosphoester and at least one antioxidant amino acid; at least one phosphoester and at least one antioxidant vitamin; at least one herbal antioxidant and at least one antioxidant mineral; at least one herbal antioxidant and at least one antioxidant amino acid; at least one antioxidant vitamin, at least one antioxidant mineral and at least one antioxidant amino acid; at least one antioxidant mineral and at least one antioxidant vitamin; at least one antioxidant amino acid and at least one antioxidant vitamin; at least one herbal antioxidant, at least one antioxidant mineral, and at least one antioxidant amino acid; at least one herbal antioxidant, at least one antioxidant mineral, and at least one antioxidant vitamin; and at least one antioxidant mineral, at least one antioxidant amino acid, and at least one antioxidant vitamin.

A primary object of this invention is to provide a composition for treatment of neurodegenerative disorders for administration to mammals that exhibits synergistic antioxidant and restorative effects on the nervous system.

A primary advantage of this invention is a lowered dosage requirement for components.

DESCRIPTION OF THE PREFERRED EMBODIMENTS (BEST MODES FOR CARRYING OUT THE INVENTION)

The present invention is a supplement combination including at least one, and preferably at least two, phosphoesters and at least one antioxidant, preferably comprising at least one but not more than five antioxidant amino acids and at least one but not more than fifteen antioxidant vitamins and at least one antioxidant mineral. These certain combinations of substances are found to give improved nervous system function with improved cognitive function and mental energy.

The composition of the present invention exhibits synergistic antioxidant and restorative effects on the nervous system effective in treating neurodegenerative disorders where oxidative injury is believed to be contributory. These synergistic effects allow use of lower doses of most of the individual components. The specific dosing limits of the present invention avoid toxic effects from elevated levels of components such as vitamin $B_2$ and selenium. Use of easily absorbed vitamin forms such as riboflavin 5' phosphate (activated vitamin $B_2$) or methylcobalamin (vitamin $B_{12}$) in the present invention also allows consistent absorption and utilization by mammals.

The composition of the present invention comprises a phosphoester. The essential phosphoester preferably comprises phosphatidylcholine, phosphatidylserine, phosphatidylethanolamine, and/or phosphatidylinositol. These compounds enhance cholinergic neurotransmission and general nerve cell membrane maintenance. The dosage of phosphatidylcholine of the present invention is preferably higher than dosages generally accepted in prior art compounds for lecithin. Combinations of phosphomonoester and/or phosphodiester compounds with enhancement compounds such as DMAE (dimethylaminoethanol), L-glutamine (a precursor of GABA, an antidepressant neurotransmitter), and succinate (Krebs cycle generation intracellular energy substrate), result in unanticipated cognitive improvement.

The composition of the present invention further comprises at least one antioxidant. The preferred antioxidants of the present invention comprise herbal, amino acid, mineral, and vitamin antioxidants. Useful, herbal antioxidants include, but are not limited to, beta carotene, various bioflavonoids (co-enzyme Q10, curcuma, ginkgo biloba (preferably an extract), ginseng (preferably American, Korean or Siberian), Gotu Kola, grape pip (proanthocyanidins), and quercetin). Useful amino acid antioxidants include, but are not limited to, L-arginine, L-glutathione, L-lysine, L-methionine, L-taurine, and L-carnitine. Useful mineral antioxidants include, but are not limited to, boron, selenium (e.g., sodium selenite and selenium methionine), manganese (e.g., citrate), magnesium (preferably elemental) and zinc. Useful vitamin antioxidants include, but are not limited to, vitamins A, B, C, E and folic acid (pteroylglutamic acid). The preferred B vitamins are $B_1$ (thiamine HCl), $B_2$ (preferably riboflavin 5'-phosphate), $B_3$ (niacinamide), $B_6$ (preferably pyridoxine HCl and activated pyridoxal 5'-phosphate), and $B_{12}$ (methylcobalamin). Other preferred vitamins are vitamin A (palminate), and vitamin E (d-alpha tocopheryl succinate). Other preferred vitamers include alpha lipoic acid, lutein, lycopene (a carotenoid), succinate, ubiquinone (co-enzyme Q10), and zeaxanthin (a yellow carotenoid). Other forms or equivalents of these stated compounds may be utilized in alternative embodiments.

Synergy and bioavailability are unique in this formulation. For example, citrus bioflavonoids are antioxidants which also synergistically increase absorption of synthetic vitamin C, helping to maintain sustained blood levels of vitamin C in the blood. Another example of a synergistic relationship is use of acetyl-L-carnitine, which works synergistically raising sustained levels of glutathione and co-enzyme Q10 Vitamin E actually diminishes the toxicity of riboflavin. (See, Free Radical Biology and Medicine 1999:24. pp. 798–808.) It should be noted that not all vitamins or other components are capable of synergistic relationships. The present invention utilizes viable synergistic relationships of at least two components of the invention, preferably utilizing at least one antioxidant, to avoid toxicity, increase activity, or maintain desired component or other chemical levels. Betaine, Bromelain, and papain are preferably added to help increase bowel absorption and thus bioavailability. Lutein and zeaxanthin are also preferably included, for their ability to specifically enhance the beneficial effects of beta carotene and vitamin A.

A correlate of synergy and bioavailability is avoidance of antagonistic interactions of components. For example, iron is not included in the formulation of the present invention because it forms free radicals responsible for oxidative stress damage. Therefore, use of iron in a supplement composition has a resultant reduction in the antioxidant properties of the composition.

The preferred formulation of the present invention is in Table 1.

TABLE 1

PREFERRED FORMULATION

| COMPONENT | DAILY DOSE (2BID) |
|---|---|
| Beta Carotene | 14,000 IU |
| Betaine anhydrous (trimethylglycine) | 250 mg |
| Bioflavonoids (lemon) | 75 mg |
| Boron Citrate | 79 mcg |
| Chromium* | 200 mg |
| Coenzyme Q10 | 30 mg |
| Bromelain* | 20 mg |
| DMAE (dimethyl amino ethanol) | 75 mg |
| Folic Acid | 180 mcg |
| Ginkgo biloba extract | 60 mg |
| Ginseng, American (15% panax quinquefolis) | 22.5 mg |
| Gotu kola* | 80 mg |
| Grape pip (proanthocyanidins) | 210 mg |
| L-Glutathione | 210 mg |
| L-Lysine | 150 mg |
| L-Methionine | 111 mg |
| L-Taurine | 75 mg |
| Lipoic acid | 45 mg |
| Lutein* | 4 mg |
| Manganese (citrate) | 27 mg |
| Magnesium oxide (elemental value) | 135.9 mg |
| Papain | 15 mg |
| Phosphatidyl Choline | 675 mg |
| Phosphatidyl Serine | 22.5 mg |
| Selenium aminoate | 17.4 mcg |
| Calcium citrate | 372 mg |
| Succinate (Calcium base soy source)* | 100 mg |
| Vitamin A (palmitate) | 5,400 IU |
| Vitamin B1 (thiamine HCl | 24.7 mg |
| Vitamin B2 (riboflavin 5'-phosphate) | 9 mg |
| Vitamin B3 (niacinamide) | 23.1 mg |
| Vitamin B5 (pantothenic calcium) | 54 mg |
| Vitamin B6 (pyridoxine HCL) | 23.1 mg |
| "Activated" Vitamin B6 (Pyridoxal 5'-phosphate) | 7.8 mg |
| Vitamin B12 (methylcobalamin) | 720 mcg |
| Vitamin C (buffered ascorbic acid) | 663 g |
| Vitamin E (d-alpha tocopheryl succinate) | 331 IU |
| Zinc (Citrate) | 49.2 mg |
| INACTIVE INGREDIENTS: | |
| Ethyl cellulose | 178.2 mg |
| Magnesium Stearate | 60 mg |
| Croscarmellose sodium | 210 mg |
| Cellulose | 1.4 gm |
| Talc | 160 mg |
| Silicon dioxide | 160 mg |

The preferred dosage range for the present invention is set forth in Table 2.

TABLE 2

PREFERRED DOSAGE RANGE OF COMPONENTS

| COMPONENT | DAILY DOSE RANGE |
|---|---|
| Acetyl-L-carnitine | 0–1,500 mg |
| Barberry | 0–7 mg |
| Beta Carotene | 0–50,000 IU |
| Betaine anhydrous (trimethylglycine) | 0–1,000 mg |
| Bilberry proanthocyanidins | 0–70 mg |
| Bioflavonoids (garlic) | 0–2 mg |
| Bioflavonoids (lemon) | 0–150 mg |
| Bioflavonoids (lime) | 0–150 mg |
| Bioflavonoids (orange) | 0–150 mg |

TABLE 2-continued

PREFERRED DOSAGE RANGE OF COMPONENTS

| COMPONENT | DAILY DOSE RANGE |
|---|---|
| Boron Citrate | 0–100 mcg |
| Chromium | 0–225 mcg |
| Coenzyme Q10 | 0–120 mg |
| Curcuma | 0–1,000 mg |
| Betaine | 0–50 mg |
| Bromelain* | 0–80 mg |
| DMAE (dimethyl amino ethanol) | 0–500 mg |
| Folic Acid | 0–250 mcg |
| Ginkgo biloba extract | 0–250 mg |
| Ginseng, American (15% panax quinquefolis) | 0–2,000 mg |
| Ginseng, Siberian | 0–400 mg |
| Gotu kola* | 0–100 mg |
| Grape pip (proanthocyanidins) | 0–1,000 mg |
| L-Glutathione | 0–2,000 mg |
| L-Lysine | 0–1,500 mg |
| L-Methionine | 0–1,500 mg |
| L-Taurine | 0–1,500 mg |
| Lipoic acid | 0–400 mg |
| Lutein* | 0–30 mg |
| Lycopene | 0–15,000 mcg |
| Manganese (citrate) | 0–50 mg |
| Magnesium oxide (elemental value) | 0–1,000 mg |
| N-acetyl-L-cystine | 0–1,500 mg |
| Papain | 0–50 mg |
| Phosphatidyl Ethanolamine | 0–500 mg |
| Phosphatidyl Choline | 0–16 gm |
| Phosphatidyl Inositol | 0–10,000 mg |
| Phosphatidyl Serine | 0–300 mg |
| Quercetin (red apple) | 0–1,000 mg |
| Quercetin (red onion) | 0–1,000 mg |
| Selenium aminoate | 0–200 mcg |
| Calcium citrate | 0–2,400 mg |
| S-adenosylmethionine | 0–800 mg |
| Succinate (Calcium base soy source)* | 0–300 mg |
| Ubiquinone | 0–600 mg |
| Vitamin A (palmitate) | 0–10,400 IU |
| Vitamin B1 (thiamine HCl) | 0–1,000 mg |
| Vitamin B2 (riboflavin 5'-phosphate) | 0–10 mg |
| Vitamin B3 (niacinamide) | 0–1,000 mg |
| Vitamin B5 (pantothenic calcium) | 0–500 mg |
| Vitamin B6 (pyridoxine HCL) | 0–500 mg |
| "Activated" Vitamin B6 (Pyridoxal 5'-phosphate) | 0–500 mg |
| Vitamin B12 (methylcobalamin) | 0–1,000 mcg |
| Vitamin C (buffered ascorbic acid) | 0–3,000 mg |
| Vitamin E (d-alpha tocopheryl succinate) | 0–800 IU |
| Zeaxanthin | 0–500 mg |
| Zinc (Citrate) | 0–100 mg |

The most preferred dosage range for the present invention is set forth in Table 3.

TABLE 3

MOST PREFERRED DOSAGE RANGE OF COMPONENTS

| COMPONENTS | DAILY DOSE RANGE |
|---|---|
| Acetyl-L-carnitine | 50–1000 mg |
| Barberry | 1–5 mg |
| Beta Carotene | 13,000–15,000 IU |
| Betaine anhydrous (trimethylglycine) | 5–50 mg |
| Bilberry proanthocyanidins | 20–50 mg |
| Bioflavonoids (garlic) | 0.1–1 mg |
| Bioflavonoids (lemon) | 50–100 mg |
| Bioflavonoids (lime) | 50–100 mg |
| Bioflavonoids (orange) | 50–100 mg |
| Boron Citrate | 50–100 mcg |
| Chromium | 175–225 mcg |
| Coenzyme Q10 | 25–50 mg |
| Curcuma | 400–600 mg |
| Betaine | 10–45 mg |
| Bromelain* | 5–50 mg |
| DMAE (dimethyl amino ethanol) | 150–250 mg |
| Folic Acid | 150–200 mcg |
| Ginkgo biloba extract | 25–100 mg |
| Ginseng, American (15% panax quinquefolis) | 5–100 mg |
| Ginseng, Siberian | 100–400 mg |
| Gotu kola* | 50–100 mg |
| Grape pip (proanthocyanidins) | 175–250 mg |
| L-Glutathione | 175–250 mg |
| L-Lysine | 100–200 mg |
| L-Methionine | 75–150 mg |
| L-Taurine | 50–100 mg |
| Lipoic acid | 5–100 mg |
| Lutein* | 5–100 mg |
| Lycopene | 5,000–15,000 mcg |
| Manganese (citrate) | 1–10 mg |
| Magnesium oxide (elemental value) | 100–200 mg |
| N-acetyl-L-cystine | 500–1000 mg |
| Papain | 5–75 mg |
| Phosphatidyl Ethanolamine | 100–350 mg |
| Phosphatidyl Choline | 500–1000 mg |
| Phosphatidyl Inositol | 500–1000 mg |
| Phosphatidyl Serine | 5–100 mg |
| Quercetin (red apple) | 100–500 mg |
| Quercetin (red onion) | 100–500 mg |
| Selenium aminoate | 5–75 mcg |
| Calcium citrate | 200–500 mg |
| S-adenosylmethionine | 300–500 mg |
| Succinate (Calcium base soy source)* | 50–150 mg |
| Ubiquinone | 300–500 mg |
| Vitamin A (palmitate) | 2500–7500 IU |
| Vitamin B1 (thiamine HCl) | 5–75 mg |
| Vitamin B2 (riboflavin 5'-phosphate) | 5–9 mg |
| Vitamin B3 (niacinamide) | 5–1000 mg |
| Vitamin B5 (pantothenic calcium) | 5–100 mg |
| Vitamin B6 (pyridoxine calcium) | 5–75 mg |
| "Activated" Vitamin B6 (Pyridoxal 5'-phosphate) | 5–75 mg |
| Vitamin B12 (methylcobalamin) | 500–1000 mcg |
| Vitamin C (buffered ascorbic acid) | 250–750 mg |
| Vitamin E (d-alpha tocopheryl succinate) | 250–750 IU |
| Zeaxanthin | 250–500 mg |
| Zinc (Citrate) | 5–100 mg |

These dosages avoid toxic effect, and the combinations act synergistically to allow lower dosing as well as to avoid antagonist interaction. Finally, the components utilized focus on reducing or eliminating neurodegenerative effects, and further, improving cognitive and memory abilities.

Although the formulation of the invention requires at least one phosphoester and at least one oxidant, any of the other components shown in the Tables may be added to the formulation, separately or in combination, preferably in the dosage ranges shown in the Tables.

Of these components, the preferred key components useful in the formulation are as follows: phosphoesters, DMAE, L-glutamine, succinate, beta carotene, bioflavonoids, L-carnitine, boron, manganese, magnesium, zinc, vitamins A, B, C, E, folic acid, and lutein.

The most preferred key components useful in the formulation are as follows: phophatidylcholine, DMAE, succinate, beta carotene, citrus biaflavinoids, and vitamin C.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A health supplement composition for mammals for improving memory and cognitive abilities comprising:
   at least one phosphoester in a daily amount of between approximately 5 mg and approximately 10,000 mg; and
   at least one herbal antioxidant comprising a daily dosage of between approximately 1 mg and approximately 5 mg of barberry, between approximately 20 mg and approximately 50 mg of bilberry proanthocyanidins, between approximately 50 mg and approximately 100 mg of lemon bioflavonoids, between approximately 50 mg and approximately 100 mg of lime bioflavonoids, between approximately 50 mg and approximately 100 mg orange bioflavonoids, between approximately 400 mg and approximately 600 mg of curcuma, between approximately 0.1 mg and approximately 1 mg of garlic bioflavonoid, between approximately 25 mg and approximately 100 mg of ginkgo biloba, between approximately 5 mg and approximately 100 mg of ginseng, between approximately 50 mg and approximately 100 mg of gotu kola, between approximately 175 mg and approximately 250 mg of grape seed proanthocyanidins, between approximately 100 mg and approximately 500 mg of red apple quercetin, between approximately 100 mg and approximately 500 mg of red onion quercetin, and between approximately 100 mg and approximately 400 mg Siberian ginseng;
   wherein said use on mammals comprises prevention or treatment of illnesses or conditions selected from the group consisting of a condition requiring memory improvement, cognitive improvement, AIDS-associated dementia, Alzheimer's disease, benign senile forgetfulness, Down's syndrome-associated dementia, Lewy body dementia, multi-infarct dementia, multiple sclerosis, Parkinson's disease-associated dementia, tardive dyskinesia, Wernicke-Korsikoff syndrome, and alcoholism-associated dementia.

2. The composition of claim 1 wherein said at least one phosphoester is selected from the group consisting of phosphatidylcholine, phosphatidylserine, phosphatidylethanolamine and phosphatidylinositol.

3. The composition of claim 1, wherein said composition comprises at least one application method selected from the group consisting of parenteral, rectal, and topical administration.

4. The composition of claim 1 wherein said phosphoester is phosphatidylcholine.

5. The composition of claim 4 wherein said phosphoester further comprises phosphatidylserine.

6. The composition of claim 4 wherein said phosphoester further comprises phosphatidylinositol.

7. The composition of claim 4 wherein said phosphoester further comprises phosphatidylethanolamine.

8. The composition of claim 1 further comprising a fatty acid.

9. The composition of claim 1 wherein said composition is administerable via an oral application method.

10. The composition of claim 4 wherein said phosphatidylcholine comprises a daily dosage of between approximately 600 mg and 700 mg.

11. The composition of claim 1 further comprising at least one amino acid.

12. The composition of claim 1 further comprising at least one mineral.

13. The composition of claim 1 further comprising at least one vitamin.

14. The composition of claim 2 further comprising at least one amino acid.

15. The composition of claim 2 further comprising at least one mineral.

16. The composition of claim 2 further comprising at least one vitamin.

17. The composition of claim 14 further comprising at least one mineral.

18. The composition of claim 14 further comprising at least one vitamin.

19. The composition of claim 18 further comprising at least one mineral.

20. The composition of claim 16 further comprising at least one mineral.

21. The composition of claim 11 further comprising at least one mineral.

22. The composition of claim 11 further comprising at least one vitamin.

23. The composition of claim 12 further comprising at least one vitamin.

24. The composition of claim 21 further comprising at least one vitamin.

25. The composition of claim 2 wherein said phosphatidylethanolamine comprises a daily dosage of between approximately 100 mg and 500 mg.

26. The composition of claim 25 wherein said phosphatidylethanolamine comprises a daily dosage of between approximately 100 mg and 350 mg.

27. The composition of claim 25 further comprising phosphatidylcholine.

28. The composition of claim 25 further comprising phosphatidylserine.

29. The composition of claim 25 further comprising phosphatidylinositol.

30. The composition of claim 25 further comprising a fatty acid.

31. The composition of claim 2 wherein said phosphatidylinositol comprises a daily dosage of between approximately 500 mg and 10,000 mg.

32. The composition of claim 31 wherein said phosphatidylinositol comprises a daily dosage of between approximately 500 mg and 1000 mg.

33. The composition of claim 31 further comprising phosphatidylcholine.

34. The composition of claim 31 further comprising phosphatidylserine.

35. The composition of claim 31 further comprising phosphatidylethanolamine.

36. The composition of claim 31 further comprising a fatty acid.

37. The composition of claim 2 wherein said phosphatidylserine comprises a daily dosage of between approximately 5 mg and 300 mg.

38. The composition of claim 37 wherein said phosphatidylserine comprises a daily dosage of between approximately 5 mg and 100 mg.

39. The composition of claim 38 wherein said phosphatidylserine comprises a daily dosage of between approximately 22.5 mg and 50 mg.

40. The composition of claim 37 further comprising phosphatidylcholine.

41. The composition of claim 37 further comprising phosphatidylethanolamine.

42. The composition of claim 37 further comprising phosphatidylinositol.

43. The composition of claim 37 further comprising a fatty acid.

44. The composition of claim 8 wherein said fatty acid is lipoic acid.

* * * * *